United States Patent [19]

Mason

[11] Patent Number: 5,536,742

[45] Date of Patent: Jul. 16, 1996

[54] ANTI-SEBORRHOEIC FORMULATION

[76] Inventor: Kenneth V. Mason, 22 Kana Crescent, Slack's Creek, Australia, 4127

[21] Appl. No.: 211,706

[22] PCT Filed: Oct. 12, 1994

[86] PCT No.: PCT/AU92/00543

§ 371 Date: Apr. 14, 1994

§ 102(e) Date: Apr. 14, 1994

[87] PCT Pub. No.: WO93/07847

PCT Pub. Date: Apr. 29, 1993

[30] Foreign Application Priority Data

Oct. 15, 1991 [AU] Australia .................. PK8926

[51] Int. Cl.⁶ ............ A61K 31/415; A61K 31/155; A61K 31/075
[52] U.S. Cl. ............ 514/398; 514/635; 514/717; 514/880; 514/881
[58] Field of Search ................. 514/252, 398, 514/635, 717, 880, 881

[56] References Cited

U.S. PATENT DOCUMENTS 4,472,421   9/1984   Büchel et al. ............ 424/273 R

OTHER PUBLICATIONS

Muller et al., *Small Animal Dermatology* (1989 Fourth Edition. W. B. Saunders Company, 718–726.

Kummel, *Color Atlas of Small Animal Dermatology* (1990) The C. V. Mosby Company, 140 and 142.

Nesbitt et al., *Dermatology for the Small Animal Practitioner—exotics feline canine* (1991) Veterinary Learning Systems Co., Inc. 63, 147–149.

Plant et al., *Factors Associated with and Prevalence of High Malassezia Pachydermatis Numbers on Dog Skin* (Sep. 15, 1992) 201(6) JAVMA, 879–882.

Power et al., *Use of Etretinate for Treatment of Primary Keratinization Disorders (idiopathic seborrhea) in Cocker Spaniels, West Highland White Terriers, and Basset Hounds* (Aug. 1, 1992) 201(3) JAVMA, 419–429.

Griffen et al, *Primary Keratinization Disorders of Dogs* (1993) Current Veterinary Dermatology, The Science and Art of Therapy Mosby–Year Book, Inc., 178–179.

Wilkinson et al., *Congenital and Hereditary Dermatoses* (1994) Color Atlas of Small Animal Dermatology—A Guide to Diagnosis– Second Edition. Mosby–Wolfe Publishing, 268–269.

Bond et al., *Comparison of Two Shampoos for Treatment of M pachydermatis—Associated Seborrhoeic Dermatitis in Basset Hounds* (1995) (36) Journal of Small Animal Practice, 99–103.

Primary Examiner—Kimberly Jordan
Attorney, Agent, or Firm—Townsend and Townsend and Crew

[57] ABSTRACT

An anti-seborrhoeic composition containing both a broad spectrum antifungal drug and a topical antiseptic is disclosed for the treatment of dogs. The composition can be formulated as a shampoo further containing a keratolytic or keratoplastic compound. The preferred antifungal drug is miconazole and the preferred topical antiseptic is chlorhexidine, and the formulation optionally contains selenium sulphide as an added ingredient.

2 Claims, 1 Drawing Sheet

ANTI-SEBORRHOEIC FORMULATION

FIELD OF THE INVENTION

THIS INVENTION relates to a composition suited to use as an anti-seborrhoeic formulation which can be for the treatment of the clinical disease seborrhoeic dermatitis in animals such as dogs.

BACKGROUND OF THE INVENTION

Seborrhoea is a chronic skin disease that is considered to be a defect in keratinization with increased scale formulation. Dandruff is a mild form. Seborrhoea is divided into three clinical forms. Seborrhoea sicca which is characterised by dry scaling of the skin. Seborrhoea oleosa is characterised by local to diffuse scaling associated with excessive sebum. Seborrhoeic dermatitis is characterised by scaling and greasiness with gross evidence of local or diffuse inflammation. There are breed predilections for Cocker Spaniels, Springer Spaniels, Basset Hounds and, in particular, the most difficult form occurs in West Highland White Terriers. It is considered to be a primary keratinization defect of genetic origin. Although some causes are known, these if found are designated secondary seborrhoeas. Primary idiopathic seborrhoeic dermatitis is currently considered to be a chronic disease that can be ameliorated but not cured.

Standard ameliorating treatments are usually shampoos containing salicylic acid, sulphur, selenium sulphide, tars and antiseptics. These give only very temporary relief from symptoms, usually for a few days at the most.

Human seborrhoeic dermatitis has recently been associated with the yeast *Malassezia (Pityrosporum) ovale*. *Malassezia packydermatis* has been reported to be associated with a dermatitis in dogs. However, dogs with the classic seborrhoeic dermatitis in West Highland Whites have been treated with ketaconazole tablets orally without producing a reliable cure. Symptoms reoccurred or worsened while on a treatment.

OBJECT OF THE INVENTION

It is an object of the invention to provide an anti-seborrhoeic formulation which is effective against seborrhoeic dermatitis achieving a therapeutic response not known before from standard treatments.

NATURE OF THE INVENTION

The invention achieves its object in provision of a composition for treatment of seborrhoeic skin disease comprising a broad spectrum anti-fungal drug and/or a topical antiseptic.

Preferably the composition is formulated for topical application and it may include a keratolytic/keratoplastic compound.

Preferably the broad spectrum anti-fungal drug is one of the imidazole/triazole group, for example miconazole.

Preferably the topical antiseptic is a phenolbiguanide type such as chlorhexidine, or tricolsan.

Preferably the keratolytic/keratoplastic compound is selenium sulphide.

Preferably the composition is provided in a shampoo base which might be any standard shampoo base and, in particular, a typical anti-dandruff shampoo base is used.

BRIEF DESCRIPTION OF THE DRAWINGS

The invention will now be described with reference to the graph of FIG. 1 which illustrates the results of a trial of a particular composition in accordance with the invention.

PREFERRED EMBODIMENTS

Figure 1:
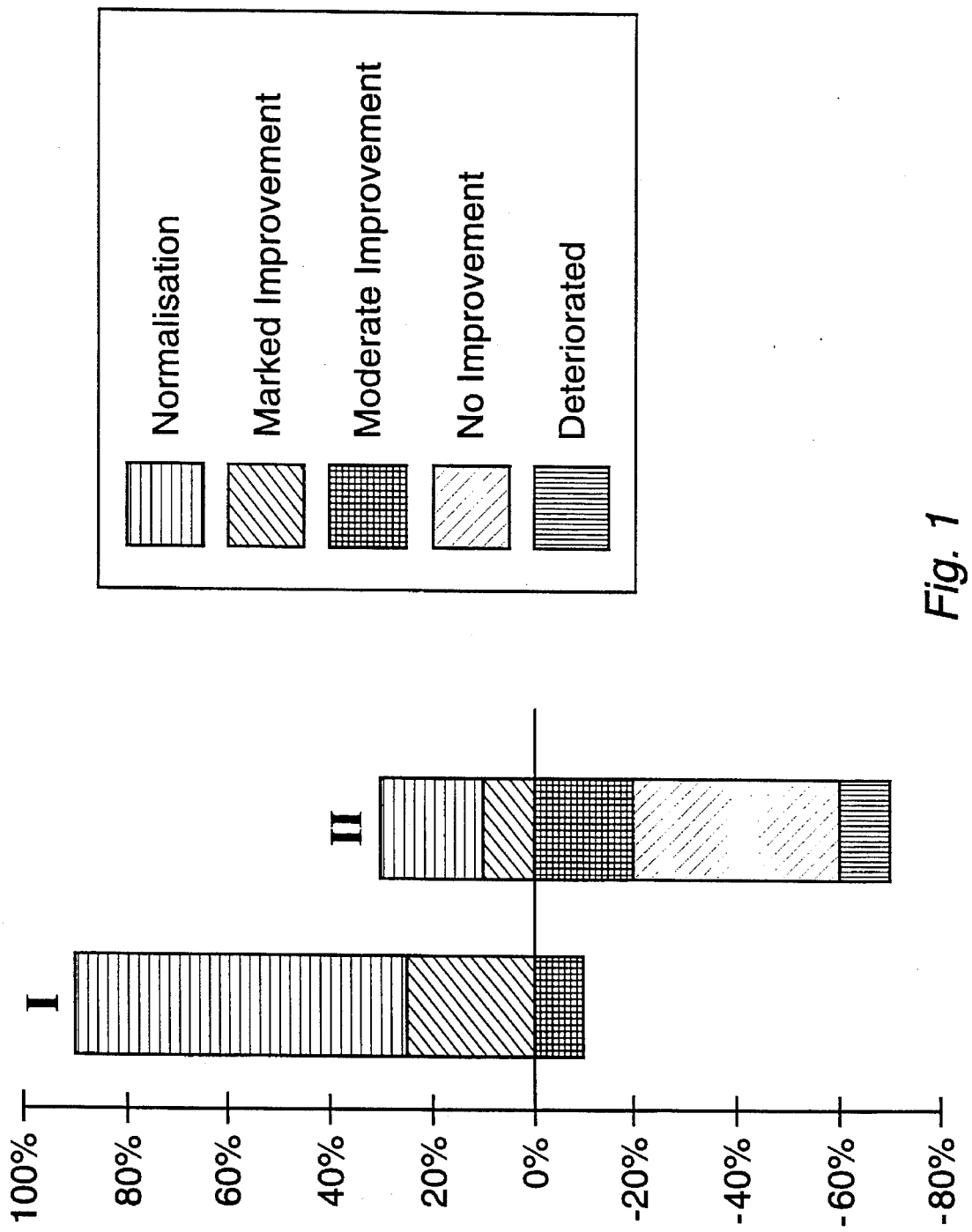

In tests of a composition in accordance with the invention, 41 dogs were diagnosed with seborrhoeic dermatitis. These 41 dogs contained a disproportional high number of West Highland White dogs as compared with the normal dog population. This is to be expected given the breed predisposition to this disease. A double blind randomised clinical trial was designed around two shampoo treatments. Cross over from one treatment group to the other was allowed if the first treatment failed.

The dogs were treated with either an industry standard 1% selenium sulphide shampoo (Selsun Blue or Seleen) originating from Abbots Laboratories or the following composition in accordance with the invention; a shampoo containing 0.25% selenium sulphide, 2.0% chlorhexidine and 2.0% miconazole. All ingredients are measured by weight. The response was then measured on an objective scale by looking for improvement in the clinical symptoms at two and four weeks.

FIG. 1 depicts graphically the results of the trial which indicates that the shampoo combination according to the invention, the graph labeled I, had results far superior to the standard treatment with a 1% selenium sulphide shampoo indicated by the graph labelled II.

Imidazole and Triazole drugs are known potent fungicide chemicals used in medicine and in agriculture. Examples are ketoconazole, miconazole, econazole and enilconazole.

One of the most potent systemic imidazole is ketoconazole. By itself, as a tablet, it has failed to provide a reliable cure in tests on seborrhoeic West Highland White dogs. Partial response in some dogs was followed by recrudescence of the seborrhoea while still on treatment.

Chlorhexidine is a phenol-related biguanide antiseptic, it is a broad spectrum anti-microbial. It has been used as a topical wash, rinse and in a shampoo in veterinary and human medicine for over 30 years. Despite being widely used, it has not gained a reputation for value in seborrhoeic dermatitis.

Selenium sulphide in a shampoo base is widely used as an anti-seborrhoeic and anti-dandruff in man and dogs. However, it gives only temporary relief. It has keratoplastic and keratolytic properties. It thus works by suppressing and breaking up scale.

Various combinations of the above active ingredients have been tried in a shampoo base on dogs with seborrhoeic dermatitis. It has been found that combinations of 1.0% selenium sulphide and 1.0% chlorhexidine; 1.0% selenium sulphide, 1% chlorhexidine and 1.0% miconazole; and 0.25% selenium sulphide, with 2% chlorhexidine and 2.0% miconazole were all much more effective than the standard 1.0% selenium sulphide alone. A 2% shampoo with imidazoles such as ketaconazole, miconazole, econazole and enilconazole also produces useful results. However, the best results have been achieved with the composition described above with reference to FIG. 1.

I claim:
1. An anti-seborrheic composition for use in the treatment of dogs, said composition comprising (a) the broad spectrum anti-fungal drug miconazole and (b) the topical antiseptic chlorhexidine.
2. An anti-seborrheic composition according to claim 1 wherein said composition is formulated as a shampoo.

* * * * *